United States Patent [19]

LaTorraca

[11] Patent Number: 4,921,642
[45] Date of Patent: May 1, 1990

[54] HUMIDIFIER MODULE FOR USE IN A GAS HUMIDIFICATION ASSEMBLY

[75] Inventor: Gary J. LaTorraca, San Diego, Calif.

[73] Assignee: Puritan-Bennett Corporation, Carlsbad, Calif.

[21] Appl. No.: 290,032

[22] Filed: Dec. 27, 1988

Related U.S. Application Data

[63] Continuation-in-part of Ser. No. 139,962, Dec. 3, 1987, abandoned.

[51] Int. Cl.$^5$ .............................................. B01F 3/04
[52] U.S. Cl. ...................................... 261/142; 261/66; 261/104; 219/272; 128/203.27
[58] Field of Search ............... 261/142, 104, 66; 219/271, 272; 128/203.27

[56] References Cited

U.S. PATENT DOCUMENTS

| | | | |
|---|---|---|---|
| 1,732,674 | 10/1929 | Dever | 261/142 |
| 3,532,270 | 10/1970 | Schoen, Jr. | 261/104 |
| 3,735,559 | 5/1973 | Salemme | 261/104 |
| 3,809,374 | 5/1974 | Schossow | 261/130 |
| 3,904,849 | 9/1975 | Lucero et al. | 261/142 |
| 3,912,795 | 10/1975 | Jackson | 261/36 |
| 3,982,095 | 9/1976 | Robinson | 219/273 |
| 4,086,305 | 4/1978 | Dobritz | 261/104 |
| 4,101,294 | 7/1978 | Kimura | 261/104 |
| 4,101,611 | 7/1978 | Williams | 261/142 |
| 4,110,419 | 8/1978 | Miller | 261/142 |
| 4,201,737 | 5/1980 | Carden | 261/142 |
| 4,284,878 | 8/1981 | Bartels | 219/272 |
| 4,288,396 | 9/1981 | Ottestad | 261/128 |
| 4,303,601 | 12/1981 | Grimm et al. | 261/142 |
| 4,430,994 | 2/1984 | Clawson et al. | 128/203.27 |
| 4,441,027 | 4/1984 | Richardson | 250/577 |
| 4,532,088 | 7/1985 | Miller | 261/142 |
| 4,612,434 | 9/1986 | Ianitelli et al. | 219/271 |
| 4,657,713 | 4/1987 | Miller | 261/142 |
| 4,715,998 | 12/1987 | Clow | 261/104 |

FOREIGN PATENT DOCUMENTS 2809802  9/1978  Fed. Rep. of Germany ...... 261/142

Primary Examiner—Tim Miles
Attorney, Agent, or Firm—Fulwider, Patton, Lee & Utecht

[57] ABSTRACT

The humidifier module for use in a gas humidification unit has a humidification chamber and a water heating chamber separated by a water vapor permeable, liquid water impermeable membrane. Gas inlet and outlet ports are provided in the humidification chamber, a water inlet port is provided for the water heating chamber, a water inlet port is provided for the water heating chamber, and a heat exchange wall is provided on one side of the water heating chamber to receive heat from a heat source in the humidification assembly. The gas humidification assembly has an enclosure adjacent the heat source, for receiving the humidifier module, a water supply source, and a controller of the heater and water supply to the humidifier module. A sensor is provided for monitoring the level of fluid within the humidification chamber, and another sensor is provided for monitoring the level of water within the water heating chamber.

35 Claims, 5 Drawing Sheets

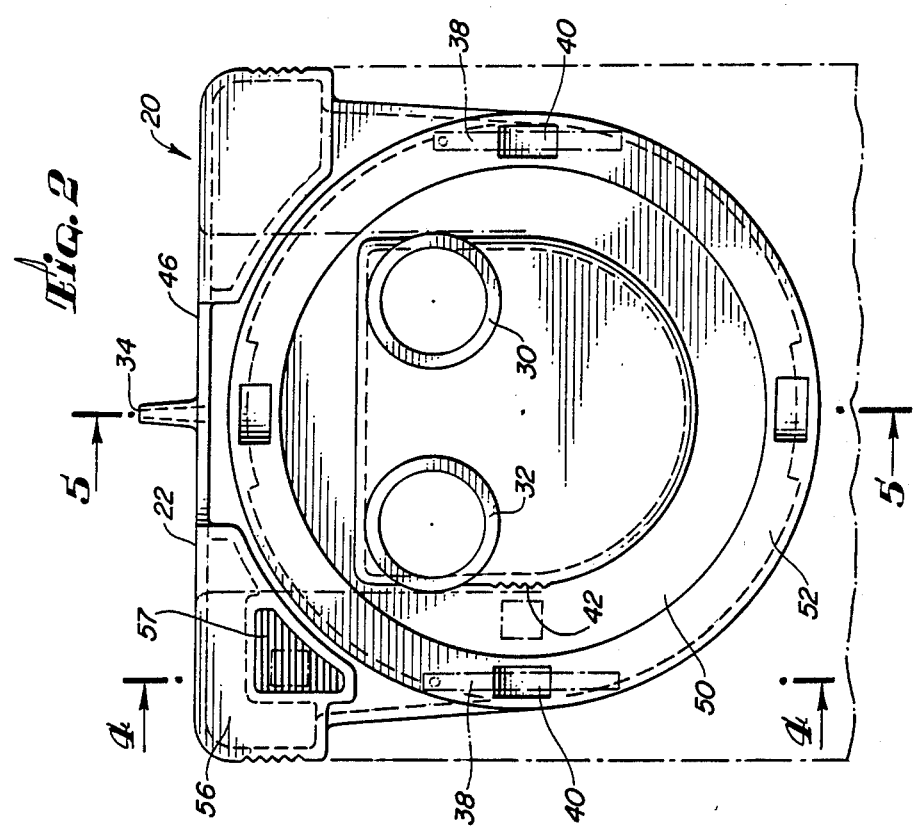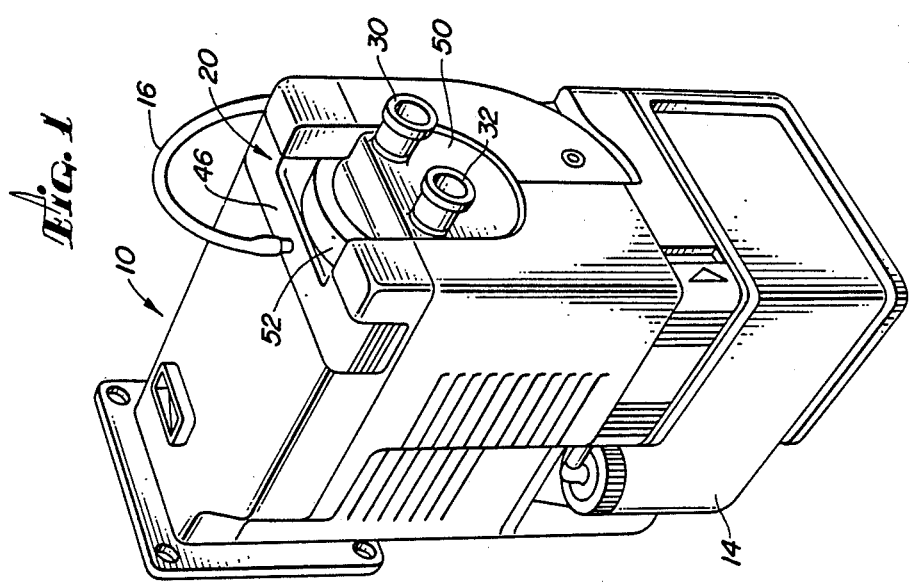

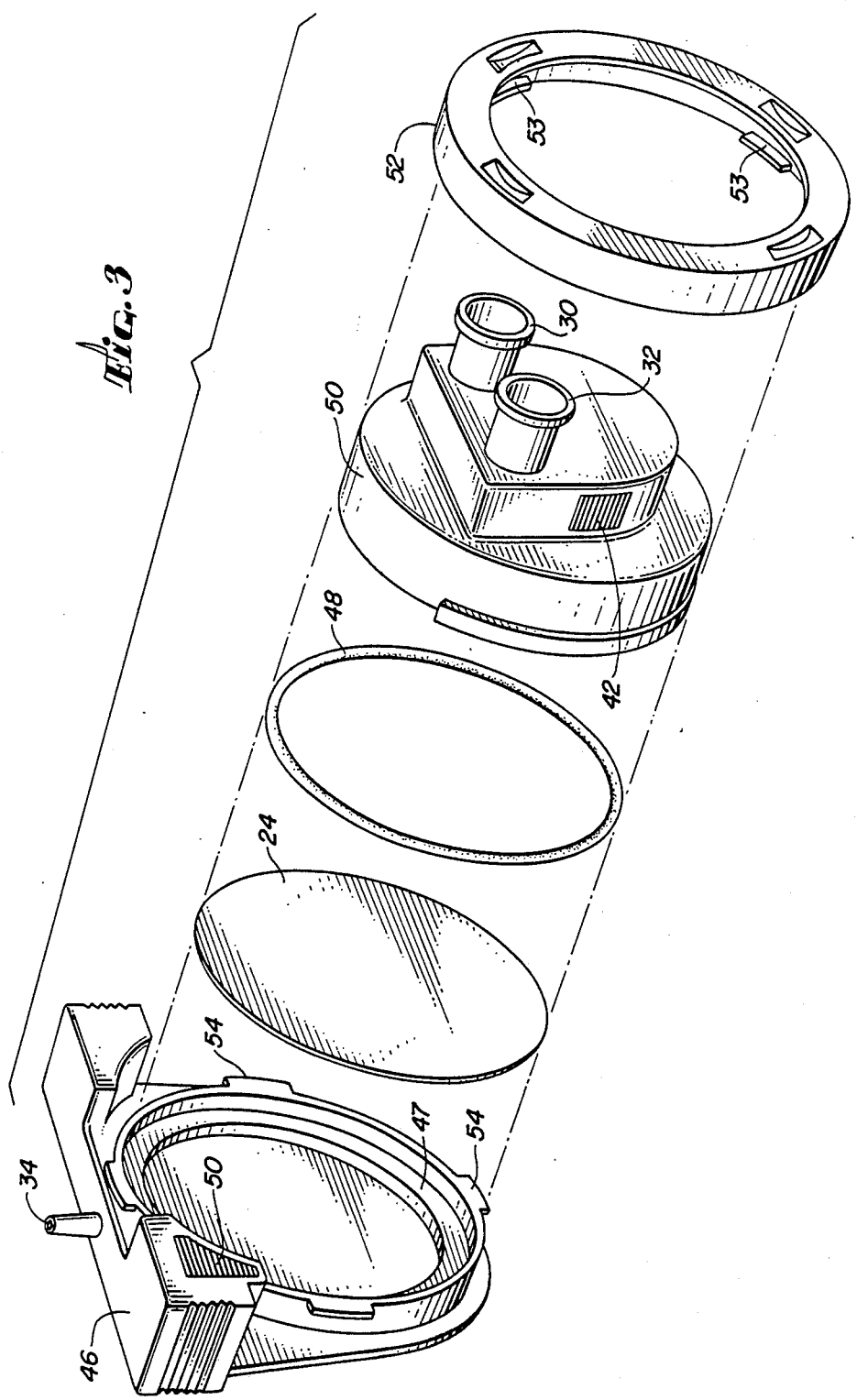

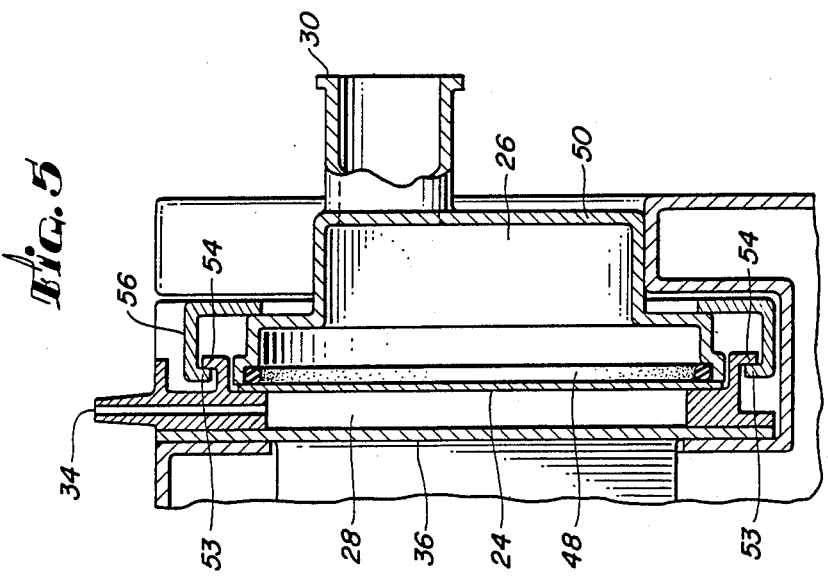
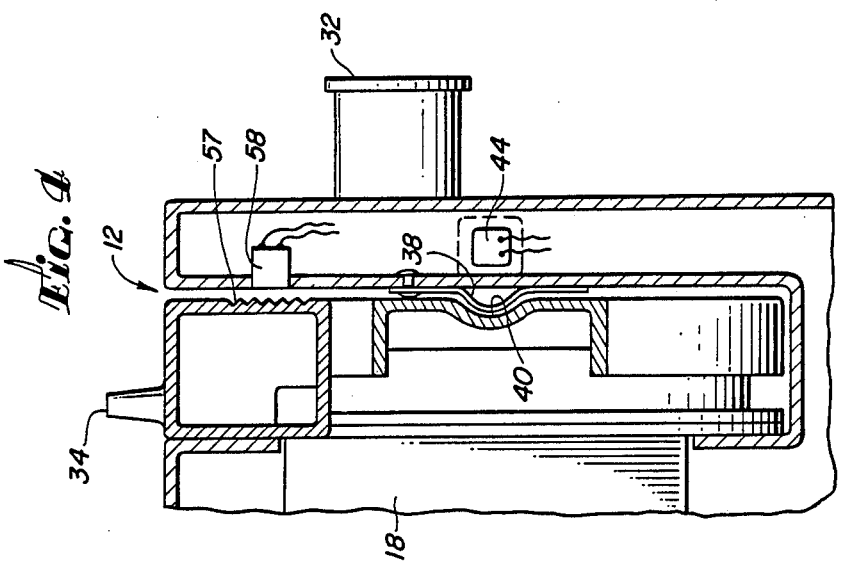

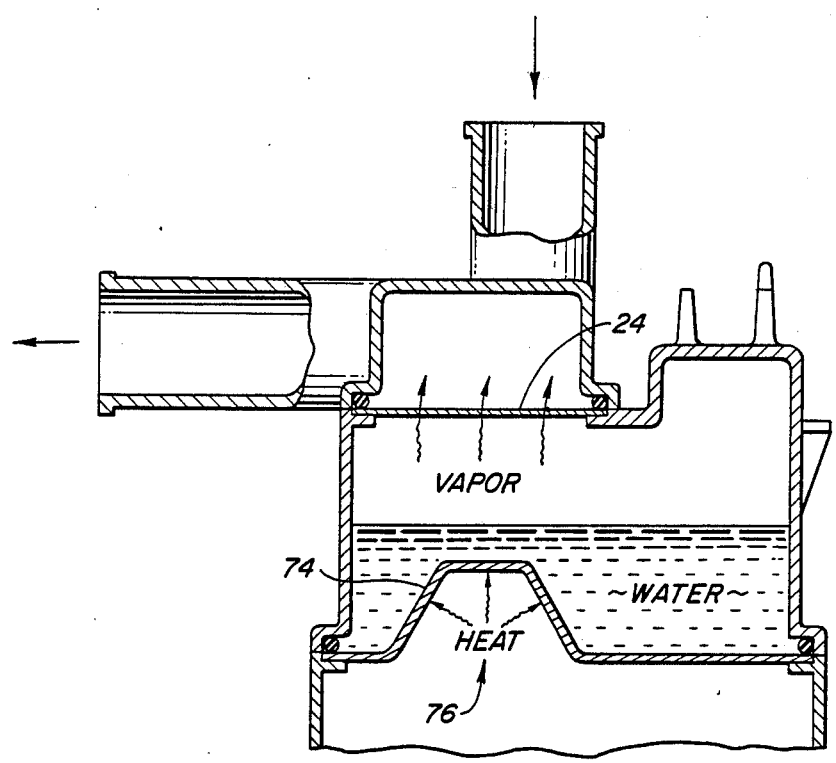

HUMIDIFIER MODULE FOR USE IN A GAS HUMIDIFICATION ASSEMBLY

BACKGROUND OF THE INVENTION

1. Related Applications

This application is a continuation-in-part of copending Ser. No. 07/139,962, filed Dec. 31, 1987.

2. Field of the Invention

This invention is directed generally to gas humidifiers, and relates more particularly to a replaceable module for use in a gas humidification assembly, and the combination of the humidifier module with the gas humidification assembly. The humidifier module may be made to be suitable for sterilization and therefore reusable, or disposable.

3. Description of Related Art

In the treatment of patients with ventilators for inhalation therapy, air may be supplied directly to the trachea, bypassing normal moistening of the air in the nose and mouth. Air for such patients is therefore generally humidified, and various technologies have been used for this purpose. In bubble humidifiers, air is bubbled through a volume of heated water, in order to add water vapor to the air. With wick humidification, air is passed over a wick which is saturated by capillary action with water, and the wick may also be heated. Steam may be created by direction of water to a heating element, or water may be nebulized or atomized with the air to be breathed by the patient, or with a supplemental gas, such as oxygen. A more modern development in materials technology takes advantage of a hydrophobic membrane which will permit the passage of water vapor. Water is vaporized and passed through the hydrophobic membrane into a humidification chamber, through which a breathable gas for the patient is circulated. The membrane has the advantage of filtering materials which might pass from the water into the air to be breathed by the patient.

A typical utilization of a hydrophobic membrane in a humidifier is described in U.S. Pat. Nos. 4,532,088 and 4,657,713, in which a supply of water is passed to a heating unit for direct heating for vaporization of the water in a vaporization chamber. The vaporization chamber is covered with a hydrophobic filter membrane which allows the water vapor, but not liquid water, to pass into an outer humidification chamber, through which breathing gas is circulated. The cover of the humidifier unit may be removed for access to the hydrophobic membrane for purposes of replacement of the humidification chamber or the membrane.

It would be desirable for a humidifier to utilize a replaceable humidifier module which does not require direct contact between the water and the surface of the heater element. The present invention satisfies this need.

SUMMARY OF THE INVENTION

The present invention provides a gas humidification assembly having a heater, an enclosure for receiving a humidifier module, a water supply source and a controller for coordinating the supply of heat and water. The humidifier module is replaceable, and may either be made to be sterilizable and reusable, or disposable. The humidifier module has a humidification chamber and a water storage and heating chamber which are separated by a water-vapor-permeable membrane. The water storage and heating chamber is heated in the humidification assembly by indirect heat exchange, and the humidifier module is quickly and easily replaceable when necessary.

Briefly and in general terms, a humidifier module for use in a gas humidification assembly having a heat source, and an enclosure for receiving the module, comprises a housing forming a hollow shell adapted to be received in the heater enclosure; a water-vapor-permeable, liquid-water impermeable membrane disposed within the housing dividing the hollow shell into a first chamber and a second chamber and forming a common wall between the first and second chambers; the first chamber comprising a humidification chamber with a gas inlet port and gas outlet port; and the second chamber comprising a water heating chamber having an inlet port and a heat exchange member formed of material capable of high heat transfer, with the heat exchange member being adapted to receive heat from the heat source within the gas humidifier assembly.

In a preferred embodiment, the humidification assembly and the humidifier module have means to detect when water or other fluid within the humidification chamber exceeds a predetermined level and to generate an alarm signal when this level is exceeded. This prevents aspiration of such fluids by the patient. The humidification assembly and humidifier module also preferably have a combination of a sensor for detecting and a means for controlling the water level in the water storage and heating chamber.

The heat exchange member of the humidifier module is designed to be exposed to a heat source in the humidification assembly, to receive heat and to provide for a high heat transfer to water within the water heating or vaporization chamber. In order to provide a high rate of heat transfer, the heat exchange member may be composed of a metal, such as aluminum, or stainless steel.

The membrane separating the vaporization chamber from the humidification chamber may be composed of a conventional hydrophobic material having pores dimensioned to permit water vapor to pass through the material, but not liquid water, at operational pressures. One such material commonly used is polytetrafluoroethylene. In the embodiment in which the humidifier module may be disassembled, the housing of the humidifier module comprises a base portion including the heat exchange member and the water inlet, and a separable vapor chamber portion which includes the gas inlet and outlet. The membrane is placed between the base portion and the vapor chamber portion and sealed to prevent liquid water from passing to the humidification chamber. The base portion and vapor chamber portion of the housing are releasably secured together, preferably with a locking ring. In an alternative embodiment in which the humidifier module is not reusable, but is rather disposable, the housing is permanently sealed with the membrane separating the water heating chamber and the humidification chamber. In either embodiment, the humidifier module is also preferably transparent to permit viewing of the humidification chamber of the humidifier module, for monitoring the liquid water level in the humidification chamber, due to condensation or leaks in the membrane, and for verification that water vapor is being produced in the humidification chamber.

The invention further generally provides for the combination of the gas humidification assembly with the humidifier module. Thus, invention further contemplates at least a portion of one or more of the snap fit connectors on the gas humidification assembly, in the enclosure, and sensors for detecting the water level in the water storage and heating chamber, and within the humidification chamber. The humidification assembly also preferably has a portion of the heater enclosure open so that the operation of the humidifier module may be viewed through the transparent housing while the humidifier is being used.

The humidification assembly also preferably contains controller circuitry for monitoring and controlling the temperature of the gas being supplied through the humidifier module, monitoring and controlling the supply of water to the water heating and storage chamber of the humidifier module, in response to the level of water in the humidifier module water storage and heating chamber. Thus, ideally, when the water level is sensed to be too low in the water heating and storage chamber, water would be supplied to the water heating chamber. Other aspects and advantages of the invention will become apparent from the following detailed description, and the accompanying drawings, illustrating by way of example the features of the invention.

BRIEF DESCRIPTION OF THE DRAWINGS

FIG. 1 is a perspective view of a humidifier module cartridge in a humidifier unit;

FIG. 2 is a front view of a humidifier cartridge;

FIG. 3 is an exploded view of one embodiment of the humidifier module;

FIG. 4 is an elevational sectional view taken along line 4—4 of FIG. 2;

FIG. 5 is an elevational sectional view taken along line 5—5 of FIG. 2;

FIG. 7 is an elevational sectional view of an alternative embodiment of a humidifier module.

DETAILED DESCRIPTION OF THE INVENTION

Figure 6:
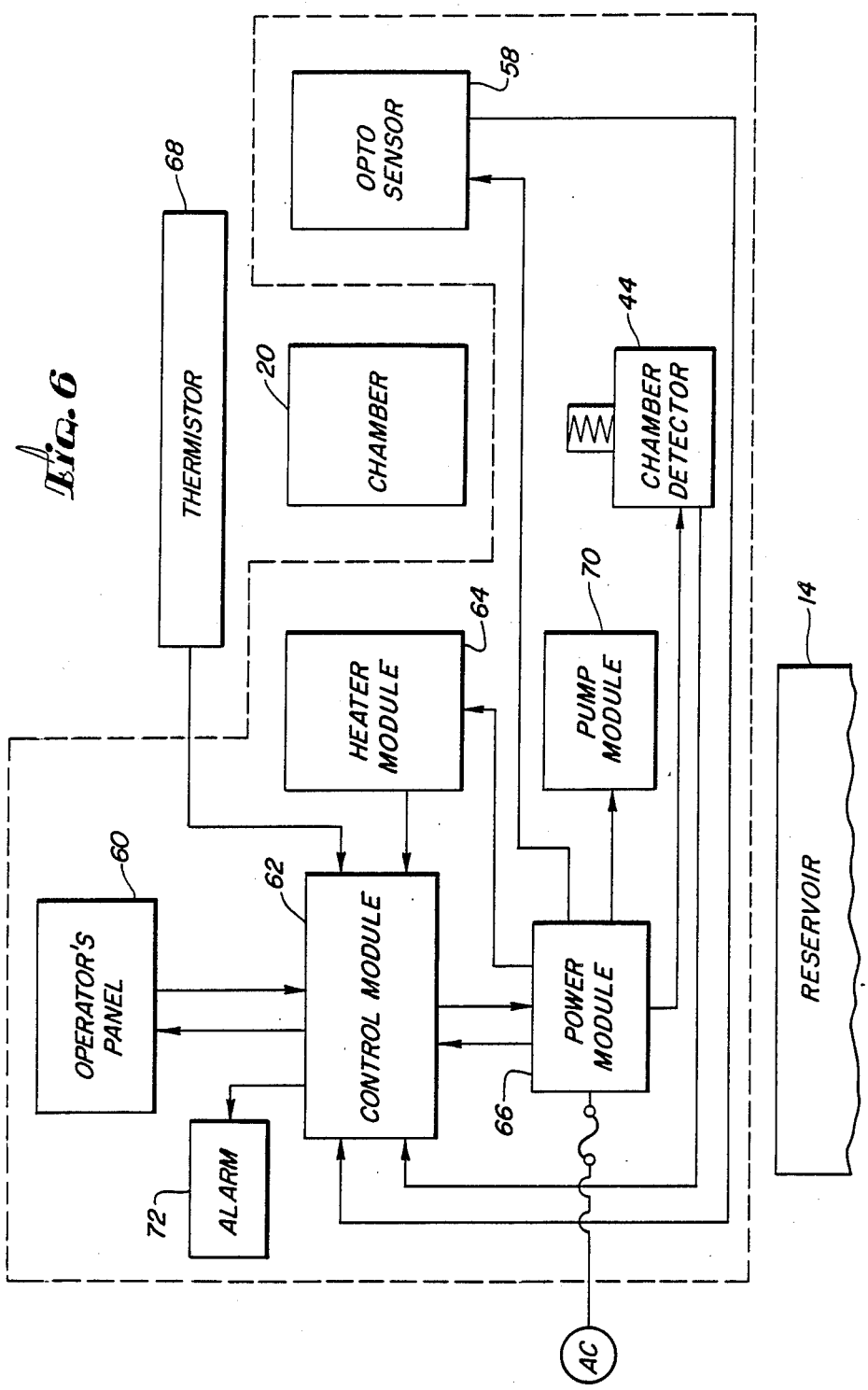
FIG. 6 is a schematic diagram of the gas humidification assembly and humidifier module.

As is shown in the drawings for purposes of illustration, the invention is embodied in a humidifier module for use in a gas humidification unit having a heat source, a water supply source, an enclosure for the humidifier module, with the module comprising a housing forming a hollow shell adapted to be received in the heater enclosure; a water vapor permeable, liquid water impermeable membrane disposed within the housing dividing the hollow shell into a first chamber and a second chamber and forming a common wall between the first and second chambers; the first chamber comprising a humidification chamber having a gas inlet port and a gas outlet port; and the second chamber comprising a water heating chamber having a water inlet port and a heat exchange member formed of a material capable of high heat transfer, the heat exchange member being adapted to receive heat from the heat source of the gas humidification unit. The humidifier module is designed to be quickly replaceable, and may be either reusable or disposable. There is a need for such a humidifier module for a humidification assembly in which heat is supplied indirectly, by way of a heat exchange member with the capability for high heat transfer, and in which a hydrophobic membrane permits only water vapor to pass therethrough.

As is shown by way of example in the drawings, the present invention includes a gas humidification assembly or unit 10 having an enclosure 12 with a heater therein. The assembly also has a water supply storage 14, with a water supply tube 16 extending from the water supply storage to a pump (not shown), and generally extending toward the heater enclosure area. Within the gas humidification assembly there is provided a heater or heat source 18 generally adjacent the heater enclosure. A humidifier module or cartridge 20 fits into the heater enclosure, for receiving heat from the heat source of the humidification unit, and for receiving a supply of water through the water supply tube.

The humidifier module generally comprises a housing 22, and a membrane 24 formed of hydrophobic material permeable to water vapor but not to liquid water, placed in the housing to separate the humidifier module into a first, humidification or vapor chamber 26, and a second, water heating or vaporization chamber 28. A suitable membrane is a polytetrafluoroethylene filter material, such as Goretex, available from W. L. Gore Associates, although other hydrophobic, microporous materials may also be suitable for such a membrane. The humidifier module also includes a gas inlet port 30, and a gas outlet port 32, allowing the gas to enter the humidification chamber, mix with the vapor, and exit as a warmed, humidified gas for breathing by a patient, or for further treatment of the gas before reaching the patient.

Provided on the top of the humidifier module is a water inlet port 34, to which a water supply tube may be connected, for receiving water from the water supply of the gas humidification unit. On one side of the humidifier module there is also provided a heat exchange member or wall 36, which may be a metal plate, to provide for the capability of high heat transfer from the heat source of the humidification unit into the water heating chamber of the humidifier module. The heat exchange wall is preferably made of aluminum, but other materials which provide high heat transfer, such as stainless steel, may be suitable as well.

Proper placement of the humidifier module in the humidification assembly is important for all of the components to cooperate together. To ensure the proper positioning of the module within the unit a snap fit connection is provided, so that when the module snaps into place, the operator can be sure that the module is in proper position with the light sources and sensors for detecting fluid level in the water storage and humidification chambers. An example of the preferred method of seating the module in the humidification unit is the provision of a spring plate or clip 38 on one side of the heater enclosure, made of spring metal and extending outward to engage an opposing indentation 40 for receiving the spring clip. One or more of these indentations may be arranged around the outside of the housing of the humidifier module, to correspond with spring plates arranged around the inside of the enclosure of the humidification unit.

There is also preferably provided a means for sensing the liquid level within the humidification chamber. Such a sensor can be an optical sensor providing a beam of light such as infrared light, to be emitted into a reflector site, which will be reflected back to a photodetector giving a logic level change when an emitted beam is either refracted or reflected, depending upon the presence of fluid in the humidification chamber. For example, as shown in the drawings, there is provided a reflector site 42 on the housing of the humidification chamber for reflecting a light beam provided by an optical sensor 44 back to the optical sensor, which also contains a photodetector for receiving the reflected light beam. As will be further described later, the light is reflected back to the photodetector when fluid in the humidification chamber is not above the level of the reflection site, and light is refracted into the fluid when the fluid rises to a level so as to surround the reflector site. The optical sensor provides a signal indicating whether fluid in the humidification chamber has risen to a predetermined level, which signal can be utilized for controlling the heat source and water supply module. It will also be appreciated that a light beam may be directed to pass through a target area of the transparent module, instead of being reflected by a reflector site, to be detected by a photodetector on the other side of the module, to provide a signal indicating the fluid level in the humidification chamber.

With reference to FIG. 3, in a preferred embodiment of the humidifier module, the housing forms a hollow shell containing the humidification chamber and the water heating chamber, and is comprised of a base portion 46 carrying the heat exchange wall and the water inlet port. The filter membrane is received over a shoulder portion 47 of the base portion of the housing to define the water heating chamber within the base portion between the membrane and the heat exchange wall. A sealing means, such as an O-ring 48 fits over the outer margin of the membrane, sealing the water heater chamber to prevent leakage of water into the humidification chamber. A vapor chamber portion 50 of the housing is also provided to fit over the O-ring and membrane onto the base portion of the housing, to define the humidification chamber of the module.

In the embodiment in which the humidifier module is sterilizable and reusable, the vapor chamber and base portions of the humidifier module may be releasably secured together by a locking ring 52 having locking tabs 53 or other means for receiving corresponding locking tabs 54 on the base portion of the housing. Rotation of the locking ring in one direction while the other components of the humidifier module are assembled will secure the vapor chamber portion to the base portion, and rotation of the locking ring in the opposite direction will release the vapor chamber portion of the housing from the base portion for disassembly. Alternatively, conventional types of spring clips bolts or screws may be utilized for releasably securing the vapor chamber portion of the housing in a sealed relationship to base portion of the housing. In the embodiment in which the humidifier module is disposable, the means for releasably securing the two portions of the housing together may be dispensed with, and the vapor chamber portion of the housing may be permanently bonded to the base portion of the housing by heat sealing, welding, conventional adhesives, or other methods commonly known to those skilled in the art.

Detection of the liquid level within the water heating chamber of the humidifier module is preferably accomplished by means of a reflector site 56 provided in the upper portion of the water heating chamber having a conical surface 57 or any other surface which provides an angled surface for reflection of light. The reflector site operates in combination with a water level optical sensor 58 positioned appropriately in the heater enclosure of the humidification unit to provide a beam of light such as infrared light, to be emitted into the reflector site, which will be reflected back to a photodetector in the optical sensor when water within the water heating chamber does not surround the reflector site. When water in the water heating chamber rises to a level so as to surround the reflector site, ideally all emitted light from the optical sensor refracts into the water, so that little or no reflected light would be detected by the photodetector of the optical sensor. As in the fluid level detection in the humidification chamber, it will be apparent that a light beam may be directed through a target area of the transparent module instead of to a reflector site, to be detected by a photodetector on the other side of the module. As will be further described later, in this manner, the optical sensor will produce a signal indicating whether water in the water heating chamber is up to the level of the reflector site, which can be utilized to control the pumping of liquid to the humidifier module by the gas humidification unit.

Referring to FIG. 6, showing a schematic diagram of the humidification assembly unit with the humidifier module or humidification chamber installed, an operator's panel 60 permits the programming of a control module 62, functioning to control the operation of the humidification unit. The control module or controller is operatively connected with a heater module 64 adjacent the heater enclosure, a power module 66, a thermistor 68, a pump module 70, and the water level optical sensor 58, or opto sensor, and the vapor chamber optical sensor 44 or chamber detector. Also shown schematically is the water supply storage or reservoir, from which the pump module supplies water to the water heating chamber of the humidifier module. Thermistor 68 monitors the temperature of the humidified gas passing from the humidifier module to the patient, producing a temperature signal received by the controller, which functions to regulate the heat source in the heater module. The signal produced by the optical sensor indicating water is not up to the level of the reflector site in the water heating chamber will be received by the controller, which functions to activate the pump module to supply water from the reservoir to the water heating chamber. When the level of water reaches the reflector site, the signal from the optical sensor is received by the controller which operates to inactivate the pump to prevent overflow of the water heating chamber and potential rupturing of the filter membrane. The vapor chamber optical sensor, indicated as the chamber detector, produces a signal indicating whether fluid has risen to a predetermined level within the humidification chamber. When the fluid is to the level of the reflector site, the light beam produced by the optical sensor is refracted into the fluid so that it is not fully reflected back by the reflector site to the photodetector of the chamber detector, altering the signal from the sensor to indicate the presence of fluid at the predetermined level in the humidification chamber, and the controller acts to activate an alarm 72.

Also, the operator may set a high temperature alarm limit via the operator panel, such that in the event of the temperature monitored by the thermistor reaching or exceeding that limit, the heater power will be shut off, and audible or visual alarms may be engaged. A thermal fuse operatively connected to the power module may also be placed in the vicinity of the heater module, to cut off the power in the event of a heater runaway, in order to prevent a fire hazard.

Referring to FIG. 7, in an alternative embodiment of the humidifier module, shown for illustrative purposes in a horizontal position, the heat exchange wall includes a portion 74 extending into the water heating chamber. The portion is in a currently preferred form of the invention formed with a frustoconical shape, for ease of manufacture but may also take a cylindrical shape, a spherical shape, or other appropriate shapes. The portion is preferably approximately symmetrically formed about the heater source 76, and most preferably the heater source is approximately equidistant from all areas of the outwardly bulging portion, for even, and more efficient heating than is generally possible with a flat plate.

From the foregoing description, it will be appreciated that the heat exchange wall of the humidifier module will provide an indirect heating of the water heating chamber, and that the humidifier module itself may be quickly and easily replaced, to permit a substantially continuous functioning of the gas humidification unit, as may be required by a patient. Further, the humidifier module itself may be made to be either sterilizable and reusable, in its most economic form, or completely disposable for convenience.

It will also be apparent that the gas humidification assembly operates in combination with and in cooperation with the humidifier module to provide the humidified gas to a patient, monitor the temperature of the gas being supplied to the patient, monitor the water level in the humidifier module and ensure minimum fluid levels in the humidification chamber. Thus, the combination of the humidifier module in the gas humidification assembly provides for automatic functioning of the unit. In addition, the transparency of the humidifier module humidification chamber allows for independent verification of the proper functioning of the unit by an operator by visual inspection.

From the foregoing, it will be appreciated that the humidifier module and combination of the humidifier module with the gas humidification assembly according to the invention provides a safe and effective humidification device which may operate automatically to provide properly humidified and temperature controlled gas to a patient, on a substantially continuous basis.

While a particular preferred form of the invention has been illustrated and described, it will be apparent that the invention is susceptible to numerous modifications and embodiments within the ability of those skilled in the art and without the exercise of the inventive faculty. Thus, it should be understood that the various changes in form, detail and application of the present invention may be made without departing from the spirit and scope of this invention.

We claim:

1. A humidifier module for use in a gas humidification assembly having a heat source, a water supply source and an enclosure for receiving said module, wherein said module comprises:
   (a) a housing forming a hollow shell adapted to be received in said enclosure;
   (b) a water-vapor-permeable, liquid-water impermeable membrane disposed within said housing dividing said hollow shell into a first chamber and a second chamber and forming a common wall between said first and second chambers;
   (c) said first chamber comprising a humidification chamber having a gas inlet port and gas outlet port; and
   (d) said second chamber comprising a water heating chamber for receiving and containing heated liquid water, said water heating chamber having a water inlet port and a heat exchange member for indirectly heating said liquid water, said heat exchange member being formed of material capable of high heat transfer, said heat exchange member being adapted to receive heat from said heat source of said gas humidifier assembly, and said membrane forming a liquid water retaining wall of said water heating chamber for permitting water vapor generated from said heated liquid water to pass from said water heating chamber to said humidification chamber, while preventing liquid water from passing from said water heating chamber to said humidification chamber.

2. The humidifier module of claim 1, wherein said housing includes means for positioning said module in heat receiving relationship with said heat source of said gas humidifier assembly.

3. The humidifier module of claim 2, wherein said means for positioning includes first means for making a snap fit connection with a mating second means for making a snap fit connection in said gas humidifier assembly.

4. The humidifier module of claim 1, wherein said housing includes a means for receiving light adapted to be in light receiving relationship with a light source in said gas humidification assembly, said means for receiving light reflecting a first amount of light when said water heating chamber contains less than a predetermined level of water and a different amount of light when water in said water heating chamber reaches said level.

5. The humidifier module of claim 1, wherein said housing includes a means for receiving light adapted to be in light receiving relationship with a light source in said gas humidification assembly, said means for receiving light reflecting a first amount of light when said humidification chamber contains less than a predetermined level of fluid and different amount of light when fluid in said humidification chamber reaches said level.

6. The humidifier module of claim 1, wherein said heat exchange member comprises a metal plate which forms a wall of the water heating chamber.

7. The humidifier module of claim 6, wherein said metal plate is aluminum.

8. The humidifier of claim 1, wherein said heat exchange member comprises a metal plate having at least a portion with a frustoconical shape projecting away from said heat source.

9. The humidifier of claim 8 wherein said heat source is disposed approximately equidistant the frustoconical portion of said metal plate.

10. The humidifier of claim 1, wherein said heat exchange member comprises a wall having at least a portion projecting away from said heat source.

11. The humidifier of claim 10, wherein said heat source is disposed approximately symmetrically distant from said wall portion projecting away from said heat source.

12. The humidifier module of claim 1, wherein said membrane comprises a polytetrarluoroethylene filter.

13. The humidifier module of claim 1, wherein at least a portion of said housing forming said humidification chamber is transparent, whereby an operator may observe fluid levels within said module.

14. The humidifier module of claim 1, wherein said housing comprises a base portion including said heat exchange member and said water inlet, and a vapor chamber portion including said gas inlet and outlet, said membrane adapted to be received in liquid water sealing relationship between said base portion and said vapor chamber portion, and said housing further comprising a means for sealably securing said base portion to said vapor chamber portion.

15. The humidifier module of claim 1, wherein said membrane is removable from said housing.

16. In combination with a gas humidification assembly having a heater, an enclosure, means for supplying water for humidifying gas, means for controlling the heater, and means for controlling a water supply, the improvement which comprises a humidifier module adapted to be seated within the enclosure having a gas inlet port and a gas outlet port for circulation of the gas through said module, said module comprising:

(a) a housing forming a hollow shell;
(b) a water-vapor-permeable, liquid-water impermeable membrane disposed within said housing and dividing said hollow shell into a vapor chamber and a water heating chamber for receiving and containing heated liquid water, said water heating chamber sharing said membrane as a common wall;
(c) said vapor chamber including said gas inlet port and said gas outlet port; and
(d) said water heating chamber having a water inlet port in communication with said water supply and a heat exchange member for indirectly heating said liquid water, said heat exchange member being formed of material capable of high heat transfer, said heat exchange member being adapted to receive heat from said heater, and said membrane forming a liquid water retaining wall of said water heating chamber for permitting water vapor generated from said heated liquid water to pass from said water heating chamber to said humidification chamber, while preventing liquid water from passing from said water heating chamber to said humidification chamber.

17. The combination of claim 16 further including means for positioning said module within the enclosure in heat receiving relationship with said heater.

18. The combination of claim 17 wherein said means for positioning includes at least one first means on said module for making a snap fit connection with at least one corresponding second means for making a snap fit connection located on said gas humidification assembly.

19. The combination of claim 16, further including a light source, a means in said module for receiving light from said light source, and a means for sensing light transmitted from said means for receiving light as a function of the presence of a predetermined level of water in the water heating chamber of said module.

20. The combination of claim 16, further including a light source, a means in said module for receiving light from said light source and a means for sensing light transmitted from said means for receiving light as a function of the presence of a predetermined level of fluid in the vapor chamber of said module.

21. The combination of claim 16, wherein said heat exchange member comprises a metal plate which forms a wall of the water heating chamber.

22. The humidifier of claim 16, wherein said heat exchange member comprises a metal plate having at least a portion with a frustoconical shape projecting away from said heater.

23. The humidifier of claim 22, wherein said heater is disposed approximately equidistant the frustoconical portion of said metal plate.

24. The humidifier of claim 16, wherein said heat exchange member comprises a wall having at least a portion projecting away from said heater.

25. The humidifier of claim 24, wherein said heater is disposed approximately symmetrically distant from said wall portion projecting away from said heater.

26. The combination of claim 16, wherein said metal plate comprises aluminum.

27. The combination of claim 16, wherein at least a portion of said housing forming said vapor chamber is transparent.

28. The combination of claim 16, wherein said module housing comprises a base portion and a vapor chamber portion, said base portion including said heat exchange member, said water inlet and said water heating chamber, and said vapor chamber portion including said vapor chamber, said membrane being adapted to be received in liquid water sealing relationship between said base portion and said vapor chamber portion, and further including a locking ring adapted to engage means for interlocking on said base portion for releasably securing said base portion and said vapor chamber portion together, with said membrane position therebetween.

29. The combination of claim 16, wherein said means for controlling said water supply is operatively connected to said water supply and is operatively connected to a sensor adapted to provide a signal to said means for controlling said water supply indicating whether there is a predetermined level of water in said water heating chamber, whereby when water in said water heating chamber is below a predetermined level said means for controlling said water supply operates to provide water from said water supply to said water heating chamber, and when water in said water heating chamber reaches said predetermined level said means for controlling said water supply operates to stop provision of water to said water heating chamber.

30. The combination of claim 16, further including a light source, a means in said module for receiving light from said light source, and a means for sensing refraction of light away from said means for receiving light as a function of the presence of a predetermined level of water in the water heating chamber of said module.

31. The combination of claim 16, further including a light source, a means in said module for receiving light from said light source, and a means for sensing refraction of light away from said means for receiving light as a function of the presence of a predetermined level of fluid in the vapor chamber.

32. The combination of claim 16, further including means for generating an alarm signal when fluid in said vapor chamber reaches said predetermined level.

33. The combination of claim 31, further including means for generating an alarm signal when fluid in said vapor chamber reaches said predetermined level.

34. The combination of claim 16, wherein said means for controlling said water supply includes an optical sensor in said humidifier assembly and a means for receiving light in said module, said means for receiving light being adapted to transmit a first amount of light to said optical sensor when said water heater chamber contains a predetermined level of water and a second amount of light when said water chamber does not contain said level of water, said optical sensor being adapted to provide a first signal to said means for controlling said water supply in response to said first amount of transmitted light and a second signal in response to said second amount of transmitted light, said means for controlling said water supply being adapted to cause water to be supplied to said water heater chamber when said second signal is received by said means for controlling said water supply.

35. The combination of claim 16, wherein said means for controlling said heater includes an optical sensor in said humidifier assembly and a means for receiving light in said module, said means for receiving light adapted to transmit a first amount of light to said optical sensor when said vapor chamber contains less than a predetermined level of fluid and a second amount of light when said vapor chamber contains said predetermined level of fluid, said optical sensor being adapted to provide a first signal to said means for controlling said heater in response to said first amount of transmitted light and a second signal in response to said second amount of transmitted light, said means for controlling said heater being adapted to cause an alarm to be activated when said second signal is received by said means for controlling said heater.

* * * * *